United States Patent [19]
Winston et al.

[11] Patent Number: 6,117,166
[45] Date of Patent: Sep. 12, 2000

[54] APPARATUS AND METHODS FOR GRAFTING BLOOD VESSEL TISSUE

[76] Inventors: Thomas R. Winston, 11700 Manor, Leawood, Kans. 66211; John M. Neet, 1762 E. 700 Rd., Lawrence, Kans. 66049

[21] Appl. No.: 08/958,179

[22] Filed: Oct. 27, 1997

[51] Int. Cl.[7] .................................................. A61F 2/06
[52] U.S. Cl. ........................................ 623/1.13; 623/1.41
[58] Field of Search ................................. 623/11, 1, 12, 623/1.13, 1.41

[56] References Cited

U.S. PATENT DOCUMENTS

| | | | |
|---|---|---|---|
| 4,990,131 | 2/1991 | Dardik et al. | 600/36 |
| 5,131,908 | 7/1992 | Dardik et al. | 600/36 |
| 5,705,732 | 1/1998 | Sims et al. | 800/2 |
| 5,747,071 | 5/1998 | Segall et al. | 424/663 |
| 5,863,296 | 1/1999 | Orton | 623/11 |
| 5,879,383 | 3/1999 | Bruchman et al. | 623/1 |
| 5,882,354 | 3/1999 | Brauker et al. | 623/11 |

OTHER PUBLICATIONS

Stefanadis, C., Toutouzas, K, et al. Stents Wrapped in Autologous Vein: An Experimental Study, Journal of the American College of Cardiology, 28(4), 1029–1–46, Oct. 1996.

Dorros, G, Jaff et al. "Percutaneous Autologous Vein Covered Palmaz Stents can Repair Arterial Tissues", Journal of the American College of Cardiology, 27(2), 191A–192A, Feb. 1996.

*Primary Examiner*—David H. Willse
*Assistant Examiner*—Suzette J. Jackson
*Attorney, Agent, or Firm*—Armstrong Teasdale LLP

[57] ABSTRACT

Apparatus and methods especially useful for facilitating grafting of healthy blood vessel tissue onto the internal wall of a blood vessel are described. In one embodiment, the apparatus includes a vascular graft secured to an expandable, wire mesh endovascular stent. The vascular graft is a partial thickness section taken through the thickness of the graft donor tissue and includes the intimal layer composed of endothelial cells. The partial thickness section facilitates regeneration of an endothelial cell layer. The vascular graft may be an autograft or homograft, and may have been prepared earlier and cryogenically frozen. The combination of stent and vascular graft is inserted into a blood vessel having damage to an internal wall. The stent is expanded in position at the site of damage, and the vascular graft grafts onto the damaged internal wall of the blood vessel while being supported by the stent. The stent also provides structural support for the blood vessel wall. The stent may be expanded with a balloon catheter inserted through the lumen of the stent. Alternate embodiments employ a variety of expandable and self-expanding endovascular stents.

26 Claims, 3 Drawing Sheets

APPARATUS AND METHODS FOR GRAFTING BLOOD VESSEL TISSUE

FIELD OF THE INVENTION

This invention relates generally to methods and apparatus for grafting blood vessel tissue, and more particularly to methods and apparatus using a stent for grafting of healthy blood vessel tissue onto an internal wall of a blood vessel.

BACKGROUND OF THE INVENTION

The number of patients undergoing treatment to open blocked, or stenosed arteries is continually increasing. There are various surgical methods to reopen the arteries, such as balloon angioplasty and rotational arthrectomy. However, practicing these methods may result in injuries to internal arterial walls which predispose the artery to scarring and restenosis. For example, about fifty percent of arteries opened with balloon angioplasty will scar to the point of restenosis.

Expensive chemical and genetic interventions to resurface internal vascular walls which have been damaged during surgery are known. Such chemical and genetic interventions methods involve both high cost and the introduction of exogenous agents which increase the risk of adverse reaction in the patient.

A less costly alternative to chemical or genetic interventions involves the use of endovascular stents. An endovascular stent is a tubular support structure which fits within the lumen of a blood vessel at a site of damage and supports the walls of the artery in their normal open configuration. The use of such stents however, is complicated by scarring around the stent from the site of damage. In addition to causing restenosis of the vessel, this scarring also may become a stimulus for thrombogenesis.

Grafting is a process in which healthy tissue is used to replace damaged tissue and reduce or eliminate scarring. The process of grafting may include taking viable tissue from an undamaged donor site on the patient herself (autograft), from another person (homograft), from another species (heterograft), using tissue which has been artificially grown or engineered, and using tissue which has been cryogenically frozen. Grafting has the general advantage that damaged tissue can literally be replaced by healthy tissue which incorporates itself with the existing healthy tissue surrounding the damaged site. The end result of a successful graft is complete tissue restoration at the injury site and reduction of scarring.

It would be desirable to provide apparatus and methods which reduce scarring and prevent restenosis in a damaged blood vessel, but which avoid the use of costly pharmaceutical agents or genetic interventions. It would further be desirable to provide apparatus and methods which employ stents in combination with grafts to support and resurface internal blood vessel walls and prevent restenosis due to scarring after vascular surgery.

SUMMARY OF THE INVENTION

These and other objects may be attained by apparatus and methods for grafting healthy blood vessel tissue onto internal walls of arteries or veins. This invention is especially useful for, but not limited to, the replacement of tissue on the internal walls of arteries which have been damaged during vascular surgery. In one embodiment, the apparatus includes a single, expandable, endovascular stent made of steel alloy wire. A vascular graft is prepared from a partial thickness section of healthy arterial or venous tissue which includes an intimal layer composed of endothelial cells. The vascular graft is meshed to facilitate migration of healthy endothelial cells from the graft to the surrounding tissue. The graft is positioned against the stent while the stent is in a compressed configuration, and attached with sutures or staples. The stent and graft combination is then inserted into a blood vessel and expanded, and the healthy tissue grafts onto the internal wall of the blood vessel.

In another aspect the present invention relates to a method for grafting healthy blood vessel tissue to a site along an internal wall of a blood vessel. In one embodiment, the method includes the steps of preparing a vascular graft from a partial thickness section of healthy blood vessel tissue, meshing the vascular graft using a tissue mesher, providing an expandable, endovascular stent, and securing the vascular graft to the stent while the stent is in a compressed configuration. To utilize the stent and graft combination, the stent and vascular graft are inserted into a blood vessel having an internal wall, the stent is expanded, and the vascular graft grafts to the internal wall of the blood vessel.

The above described invention provides apparatus and methods useful for grafting healthy blood vessel tissue onto an internal blood vessel wall. This invention is especially useful in the treatment of damaged internal arterial walls to reduce the occurrence of scarring and restenosis after vascular surgery. This invention combines the advantages of stents and grafts and avoids the use of costly pharmaceutical agents or genetic interventions.

DETAILED DESCRIPTION

The present invention is directed to apparatus and methods for grafting healthy blood vessel tissue onto an internal wall of a blood vessel. Although specific embodiments of the apparatus and methods are described below, many variations and alternatives are possible. Also, the term vascular graft as used herein refers to vascular tissue which comes from a patient's own healthy arteries or veins, homograft tissue from another person's arteries or veins, tissue which has been cryogenically frozen, heterograft tissue which comes from a species other than human, and to tissue which has been artificially grown or engineered. The term endovascular stent as used herein refers to wire mesh stents, compressed wire stents, roll type stents, coil type stents, and any expandable endovascular stent.

The present invention is especially useful for, but not limited to, grafting healthy replacement blood vessel tissue at a site of damage on an internal arterial wall which has been damaged during vascular surgery. The present invention is also useful for grafting healthy blood vessel tissue to an internal blood vessel wall.

Figure 1:
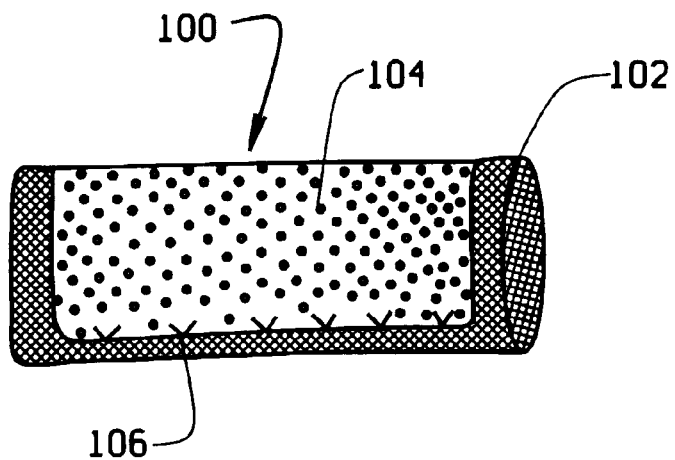
FIG. 1 is a schematic illustration of an apparatus for grafting healthy blood vessel tissue onto the internal wall of a blood vessel.

Referring specifically to the drawings, FIG. 1 is a schematic view of an apparatus 100 for grafting healthy blood vessel tissue onto an internal wall of a blood vessel. Apparatus 100 includes an expandable endovascular stent 102, and a vascular graft 104 positioned against stent 102. Vascular graft 104 is secured to endovascular stent 102 using surgical sutures 106. Surgical sutures 106 may be composed of either permanent or resorbable suture material. Alternatively, surgical staples may be used to secure vascular graft 104 to stent 102. Endovascular stent 102 includes wire mesh having interstices and configured in tubular form. Wire mesh stent 102 is fabricated from a steel alloy such as Nitinol, Elgiloy, or 304 stainless steel. Expandable, wire mesh, endovascular stents are available from surgical supply companies, including Johnson & Johnson Medical Inc., Arlington, Tex., and Medtronic, Inc., Minneapolis, Minn.

To prepare vascular graft 104, and in one embodiment, a tubular section of healthy artery is surgically removed from a donor site. The section is sized to fit within the dimensions of endovascular stent 102 in the compressed configuration. Using procedures known to those of ordinary skill in the art of tissue grafting, a single longitudinal cut through one wall of the section is made to allow the tubular section of healthy artery to open and form a sheet. A dermatome, known to those of ordinary skill in the art, is used to make a partial thickness section from the sheet of tissue. The partial thickness section includes an intimal layer of the blood vessel tissue, composed of endothelial cells. The partial thickness section may also include portions of the medial and adventitial layers of the blood vessel tissue.

The use of a partial thickness section improves the viability of vascular graft 104 by improving access of vascular graft 104 to established blood supply routes within tissue composing a blood vessel being treated. The partial thickness section also facilitates migration of healthy endothelial cells from vascular graft 104 to a site of damage on the blood vessel internal wall. Homograft versions of vascular graft 104 may have been prepared well in advance of a procedure, cryogenically frozen in liquid nitrogen, and preserved indefinitely before use for vascular graft 104. Cryogenically preserved homografts are known to those of ordinary skill in the art and are commercially available from, for example, the Cryolife Company, Marietta, Ga. It is believed that the process of cryogenically freezing graft tissue reduces the risk of graft rejection in the patient by inactivating or eliminating tissue antigens.

In another embodiment, vascular graft 104 is modified by using a tissue mesher. The tissue mesher, known to those skilled in the art of tissue grafting, is used to form a meshed vascular graft. The meshed vascular graft is used in the same manner as graft 104 but provides increased expanding capacity. The increased capacity of the meshed vascular graft to expand affords greater and more flexible coverage than does a solid vascular graft. Meshing of the vascular graft also enhances the mobility of cells in the endothelial layer, which facilities migration of cells to the site of damage on the blood vessel wall. An alternate modification of vascular graft 104 is to prepare multiple strip vascular grafts instead of a single solid sheet.

Figure 2:
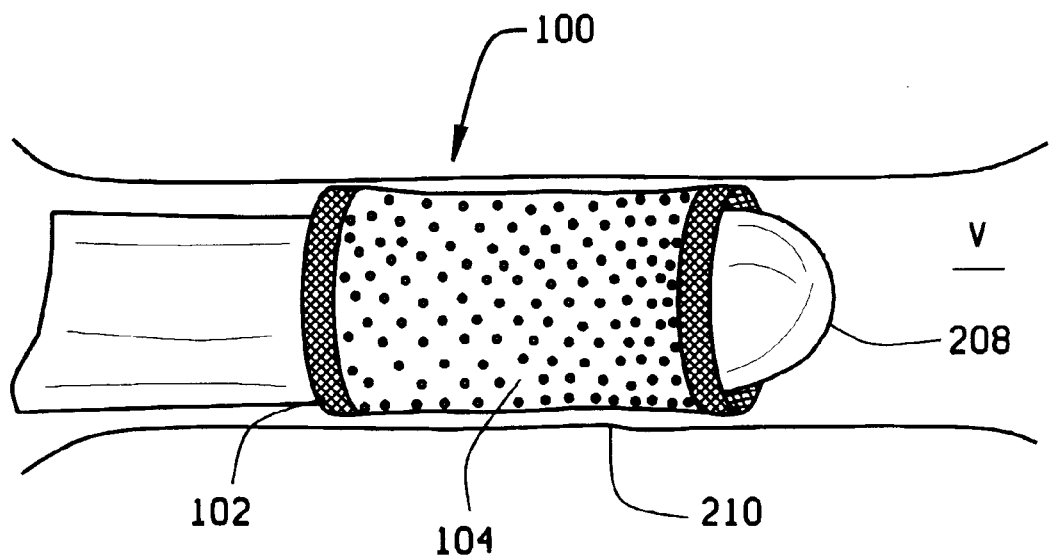
FIG. 2 is a schematic illustration of the apparatus shown in FIG. 1 and positioned within a blood vessel having an internal wall.

FIG. 2 is a schematic illustration of apparatus 100 shown in FIG. 1 and positioned within a blood vessel having an internal wall. Vascular graft 104 is positioned against and secured to endovascular stent 102 with surgical sutures 106. A balloon catheter 208, commonly used for angioplasty and commercially available, is inserted through the lumen of endovascular stent 102. Balloon catheter 208 is used to position apparatus 100 within a blood vessel V at a site of damage 210. Balloon catheter 208 is then inflated and used to expand endovascular stent 102, thereby pressing vascular graft 104 onto the walls of blood vessel V and covering damaged site 210 with vascular graft 104. Balloon catheter 208 is then deflated and withdrawn, leaving vascular graft 104 supported by endovascular stent 102 in place within blood vessel V.

Figure 3:
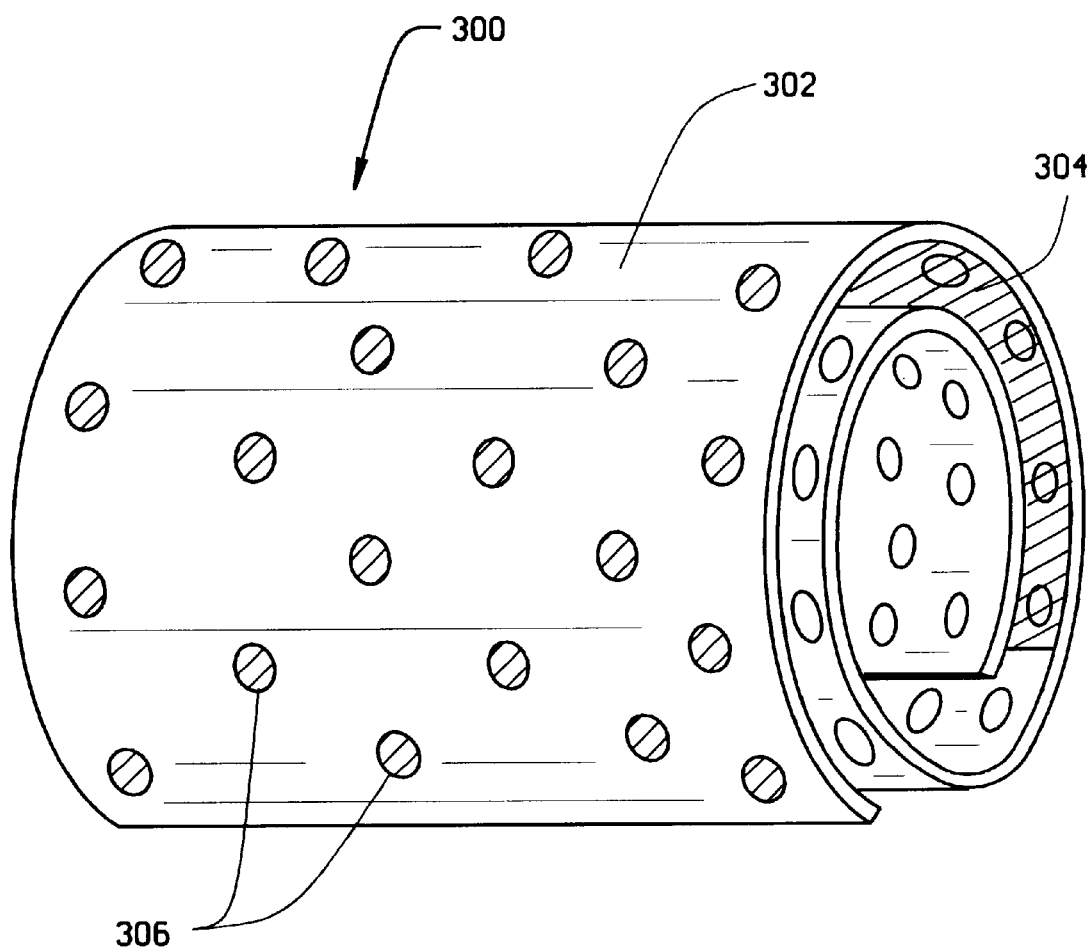
FIG. 3 is a schematic illustration of an apparatus for grafting healthy blood vessel tissue onto the internal wall of a blood vessel in accordance with another embodiment of this invention.

FIG. 3 is a schematic illustration of an apparatus 300 in accordance with another embodiment of this invention. Apparatus 300 includes a roll type stent 302. Roll type stents are commercially available from Cardiovascular Dynamics, Inc., Irvine, Calif. and can be modified to include perforations 306. Specifically, stent 302 is a flexible, steel alloy sheet wound in a multiple layer roll. Roll type endovascular stent 302 has a plurality of perforations 306. A vascular graft 304 is positioned against the internal surface of the outermost layer of roll type stent 302 and held in place using surgical sutures or surgical staples (not shown).

In use, and before insertion into a blood vessel, stent 302 is maintained in a compressed diameter configuration with the multiple layers of stent 302 in close juxtaposition with one another and vascular graft 304 rolled in between the outermost and next outermost layers of stent 302. After insertion, stent 302 is allowed to unwind and expand, thereby supporting the outermost layer of stent 302 against the internal wall of the blood vessel. In doing so, stent 302 brings vascular graft 304 directly in contact with the internal walls of the blood vessel at perforations 306 through stent 302. Healthy endothelial cells from vascular graft 304 can migrate directly through perforations 306 to meet one another and to a site of damage. This enhances the ability of vascular graft 304 to form a substantial interface of healthy tissue between a damaged site and blood flow within the vessel. It is believed that a healthy tissue interface along the internal vessel wall reduces the risk of thrombogenesis.

Alternatively, an expandable steel alloy stent in the form of wire mesh, compressed wire or coiled wire may be substituted for perforated roll type stent 302. Vascular graft 304 may be in solid sheet or meshed form and is positioned against the internal surface of expandable stent 302 while stent 302 is in a compressed, reduced size configuration. Vascular graft 304 is secured to stent 302 using surgical sutures or surgical staples. Once in place at the site of damage within a blood vessel, expandable stent 302 is allowed to expand. After expansion, the interstices in a wire mesh stent, the spaces between individual coils in a coil type stent, or spaces between individual wires in a compressed wire type stent, serve a function similar to that of perforations 306, allowing migrating endothelial cells more direct access to each other and to the site of damage.

In an alternate embodiment of the apparatus, vascular graft 304 is positioned against the external surface of the outermost layer of perforated, roll type, endovascular stent 302. The apparatus is practiced in much the same way as described above but results in a different final configuration of vascular graft 304 relative to the blood vessel wall and to stent 302. When roll type endovascular stent 302 is allowed to expand from the initially compressed configuration, stent 302 supports vascular graft 304 directly against the blood vessel wall, initially leaving stent 302 itself as the interface between the vessel wall with vascular graft 304, and blood flow within the vessel. It is believed that endothelial cells from the intimal layer of vascular graft 302 can migrate through perforations 306 and over time form a layer of endothelial cells substantially covering the internal surface of the outermost layer of roll of stent 302. Alternatively, a roll type stent without perforations may be used so that endothelial cells migrate around the edges of stent 302 and form a new endothelial lining along the internal surface of stent 302.

Figure 4:
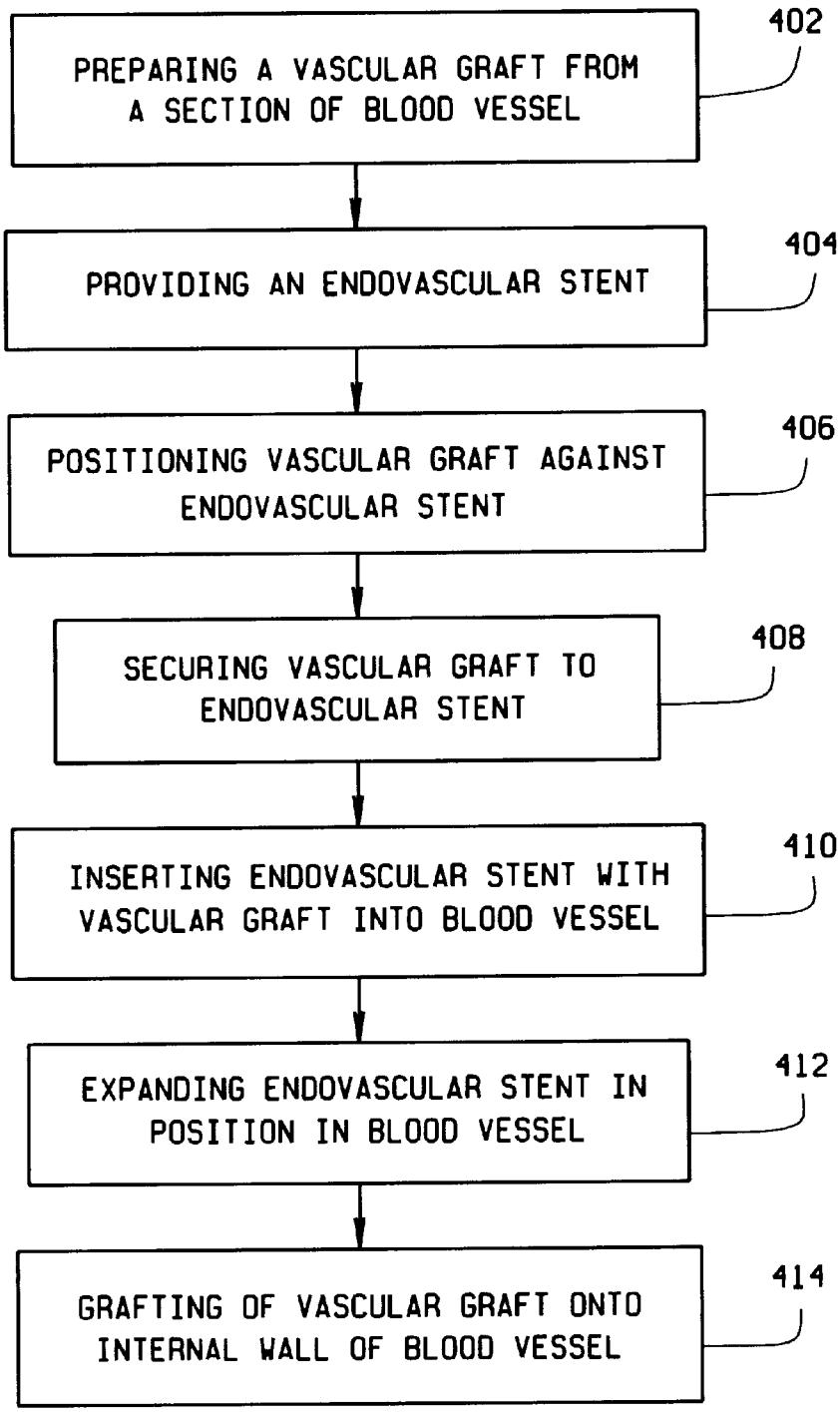
FIG. 4 is a flow chart illustrating a method for grafting healthy blood vessel tissue onto the internal wall of a blood vessel.

In another aspect, the present invention relates to a method for grafting healthy tissue onto a blood vessel having damage to an internal wall. FIG. 4 is a flow chart illustrating a method 400 for using a stent to facilitate grafting onto an internal wall of a blood vessel. Method 400 includes preparing a vascular graft from a section of blood vessel tissue 402. Particularly, step 402 includes forming a sheet from the tissue section, for example by making a single longitudinal cut to open up the tubular shape of the section. Using a dermatome, a partial thickness section is made through the thickness of the tissue while leaving the intimal layer intact. The adventitial layer is partially or completely removed. Additionally, step 402 may be practiced by making a mesh or separate multiple strips of the vascular graft. After preparation of the vascular graft 402, an endovascular stent is provided 404, and the graft is positioned against the stent 406. The graft is secured to the stent 408 using, for example, surgical sutures or staples.

The stent and the vascular graft are inserted into a blood vessel having an internal wall 410. The stent is then used to position the vascular graft and expanded 412, and then the vascular graft grafts onto the internal wall of the blood vessel 414. Method 400 may be practiced using a balloon catheter inserted through the stent to insert the stent into the blood vessel 410. In addition, step 412 may be practiced using the balloon catheter to expand an expandable stent and support the vascular graft against the internal wall of the blood vessel. Alternatively, a self-expanding stent such as a coil, roll, or compressed wire type stent may be used to support the vascular graft against the internal wall of the blood vessel after insertion into a blood vessel.

Using the above described apparatus and methods, vascular graft tissue can be used to resurface the internal walls of blood vessels. In particular, this invention is useful for the replacement of arterial tissue damaged during vascular surgery. The combination of endovascular stent and vascular graft provides both structural support for the blood vessel and replacement of damaged tissue with healthy tissue, thereby reducing the risks of post-surgery restenosis and thrombogenesis.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. Apparatus comprising:
   an endovascular stent; and
   a vascular graft comprising a first partial thickness section of a full thickness of blood vessel tissue, the blood vessel tissue having an intimal layer, a medial layer and an adventitial layer, wherein said first partial thickness section comprises at least a portion of the intimal layer wherein at least a portion of the adventitial layer has been removed and a second partial thickness section includes at least a portion of the adventitial layer, said vascular graft positioned against said endovascular stent.

2. Apparatus in accordance with claim 1 wherein said first partial thickness section further comprises at least a portion of the adventitial layer.

3. Apparatus in accordance with claim 1 wherein said endovascular stent comprises an expandable wire mesh stent.

4. Apparatus in accordance with claim 1 wherein said endovascular stent is expandable and comprises a thin flexible sheet having perforations therethrough.

5. Apparatus in accordance with claim 1 wherein said vascular graft comprises meshed tissue.

6. Apparatus in accordance with claim 1 wherein said vascular graft comprises a plurality of strips of blood vessel tissue.

7. Apparatus in accordance with claim 1 wherein said vascular graft comprises autograft tissue.

8. Apparatus in accordance with claim 7 wherein said vascular graft comprises arterial tissue.

9. Apparatus in accordance with claim 7 wherein said vascular graft comprises venous tissue.

10. Apparatus in accordance with claim 1 wherein said vascular graft comprises homograft tissue.

11. Apparatus in accordance with claim 10 wherein said vascular graft has been cryogenically frozen.

12. Apparatus in accordance with claim 1 further comprising a plurality of surgical sutures securing said vascular graft to said endovascular stent.

13. Apparatus in accordance with claim 1 further comprising a plurality of surgical staples securing said vascular graft to said endovascular stent.

14. Apparatus in accordance with claim 1 wherein said endovascular stent is a balloon-expandable stent having a lumen.

15. Apparatus in accordance with claim 14 further comprising a balloon catheter inserted through the lumen of said balloon-expandable stent.

16. Apparatus in accordance with claim 1 wherein said stent is a self-expanding roll type stent.

17. A method comprising the steps of:
    obtaining a tubular section of blood vessel;
    making a longitudinal cut through a wall of the tubular section forming a sheet of full thickness blood vessel tissue having an intimal layer, a medial layer and an adventitial layer;
    forming a first partial thickness section and a second partial thickness section, wherein the first partial thickness section comprises at least a portion of the intimal layer, the first partial thickness section forming a vascular graft wherein at least a portion of the adventitial layer has been removed;
    positioning the vascular graft against an expandable endovascular stent; and
    securing the vascular graft to the endovascular stent.

18. A method in accordance with claim 17 wherein forming the first partial thickness section comprises the step of forming a second partial thickness section including at least a portion of the adventitial layer.

19. A method in accordance with claim 17 further comprising the step of securing the vascular graft to the endovascular stent using surgical sutures.

20. A method in accordance with claim 17 further comprising the step of securing the vascular graft to the endovascular stent using surgical staples.

21. A method in accordance with claim 17 wherein forming the first partial thickness section comprises the step of forming a solid sheet from the first partial thickness section.

22. A method in accordance with claim 17 further comprising the step of forming a mesh from the first partial thickness section.

23. A method in accordance with claim 17 further comprising the step of forming a plurality of strips from the first partial thickness section of blood vessel tissue.

24. A method in accordance with claim 17, further comprising the steps of:
- inserting the endovascular stent in combination with the vascular graft into a blood vessel having an internal wall; and
- expanding the stent so that the vascular graft grafts to the internal wall of the blood vessel.

25. A method in accordance with claim 24 wherein providing a stent comprises the step of providing a balloon expandable stent and wherein expanding the stent comprises the step of expanding the balloon expandable stent to support the vascular graft against the internal wall of the blood vessel.

26. A method in accordance with claim 24 wherein providing a stent comprises the step of providing a self-expanding roll type stent and wherein expanding the stent comprises the step of allowing the self-expanding roll type stent to expand and to press the vascular graft against the internal wall of the blood vessel.

* * * * *